US00PP27735P3

(12) United States Plant Patent
Coakley

(10) Patent No.: US PP27,735 P3
(45) Date of Patent: Feb. 28, 2017

(54) ***DELPHINIUM* PLANT NAMED 'COADELCHA'**

(50) Latin Name: ***Delphinium* hybrid**
Varietal Denomination: Coadelcha

(71) Applicant: Anthony Paul Coakley, Glasgow (GB)

(72) Inventor: Anthony Paul Coakley, Glasgow (GB)

( * ) Notice: Subject to any disclaimer, the term of this patent is extended or adjusted under 35 U.S.C. 154(b) by 77 days.

(21) Appl. No.: 14/545,217

(22) Filed: Apr. 7, 2015

(65) Prior Publication Data

US 2016/0302343 P1 Oct. 13, 2016

(51) Int. Cl.
*A01H 5/02* (2006.01)

(52) U.S. Cl.
USPC ..... Plt./423

(58) Field of Classification Search
USPC ..... Plt./423
See application file for complete search history.

*Primary Examiner* — Keith Robinson
(74) *Attorney, Agent, or Firm* — Samuel R. McCoy, Jr.

(57) ABSTRACT

'Coadelcha' is a distinctive variety of *Delphinium* which is characterized by the combination of flowers with a large quantity of petaloids, tepals and petaloids with a unique color combination of dark purple and blue an upright plant habit, a vigorous rate of growth, and the stability and uniformity of these traits through successive cycles of asexual propagation. The new cultivar produces a strong main flowering stem as well as a free and continuous bloom habit from early through late summer.

1 Drawing Sheet

Latin name of the genus and species: The Latin name of the genus and species of the novel variety disclosed herein is *Delphinium* hybrid.

Variety denomination: The inventive variety of *Delphinium* disclosed herein has been given the variety denomination 'Coadelcha'.

BACKGROUND OF THE INVENTION

The present invention relates to a new and distinct cultivar of *Delphinium*, which has been given the variety denomination of 'Coadelcha'. Its market class is PLT/423. The genus *Delphinium* is commonly known as a member of the Ranunculaceae family and may also be referred to as Larkspur. *Delphinium* plants bear inflorescences of a showy spike or racemes that may sometimes be paniculate and contain few to many flowers on erect and sometimes branching stems. The genus *Delphinium* is unusual in that all three primary colors are represented in different species. The tall hybrids with their long spikes are available in a wide range of colors including purple, mauve, pink, white, and cream as well as varying shades of blue. In Europe, they are grown as perennials but are treated as annuals in California and regions of similar climate.

Parentage: The *Delphinium* variety 'Coadelcha' is the result of a planned breeding program carried out in Glasgow, Scotland. 'Coadelcha' is a seedling selection which resulted from the controlled pollination of two proprietary *Delphinium* hybrid breeding accessions (unnamed, uncommercialized and undistributed) developed and owned by the inventor. The initial selection of the cultivar now known as 'Coadelcha' was made in August of 2008. At that time it was determined that said cultivar exhibited certain distinguishing characteristics that would prove favorable for commercial production and marketability.

Asexual Reproduction: 'Coadelcha' was first asexually propagated by tissue culture in 2012 at a tissue culture laboratory in Roelofarendsveen, The Netherlands under the control of the inventor. The distinctive characteristics of the inventive 'Coadelcha' cultivar are stable from generation to generation; clones of the cultivar produced by tissue culture maintain the distinguishing characteristics of the original plant.

SUMMARY OF THE INVENTION

The following characteristics have been repeatedly observed and represent the distinguishing characteristics of the new *Delphinium* cultivar 'Coadelcha'. These traits in combination distinguish 'Coadelcha' as a new and distinct cultivar.

1. *Delphinium* 'COADELCHA' exhibits a floret with a high tepal and petaloid count.
2. *Delphinium* 'COADELCHA' exhibits a unique color combination within the floret.
3. *Delphinium* 'COADELCHA' exhibits an upright growth habit.
4. *Delphinium* 'COADELCHA' exhibits a high degree of plant vigor.
5. *Delphinium* 'COADELCHA' exhibits a primary inflorescence with a strong peduncle.
6. *Delphinium* 'COADELCHA' exhibits a freely and continuous bloom habit.

BRIEF DESCRIPTION OF THE FIGURES

The Figure shows, as nearly true as it is reasonably possible to make the same in color illustrations of this type, an exemplary specimen of the new cultivar 'Coadelcha', at 9 months old, in a one liter nursery pot. The plant shown was grown outdoors in Glasgow, Scotland using conventional production practices typically employed for producing *Delphinium* plants. No disease or pest measures were taken in producing this plant.

BOTANICAL DESCRIPTION OF THE PLANT

The following is a detailed botanical description of a new and distinct variety of *Delphinium* known as 'Coadelcha', based upon observations of plants, approximately 9 months, grown outdoors in Glasgow, Scotland from winter to summer. The temperature during this time period ranged from 5 to 17 degrees Celsius at night to 14 to 28 degrees Celsius during the day. Observation data was recorded in August of 2014.

Those skilled in the art will appreciate that certain characteristics will vary with older or, conversely, with younger plants. 'Coadelcha' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2007 edition.

A botanical description of 'Coadelcha' and comparisons with other varieties of *Delphinium* are provided below.

TECHNICAL DESCRIPTION OF THE VARIETY

Plant description:

*Growth rate*.—Vigorous.

*Growth habit*.—Upright herbaceous perennial with flowers arranged on terminal racemes; numerous racemes per plant.

*Height*.—95.0 cm in height.

*Width*.—Approximately 60.0 cm.

*Environmental tolerances*.—Tolerates temperatures as low as approximately −20 degrees Celsius (twenty degrees below freezing); upper temperature tolerance is unknown. No tolerance for drought.

*Propagation*.—Tissue culture.

*Time to produce a rooted cutting*.—Approximately 4 to 5 weeks to produce a rooted cutting.

*Disease and pest resistance*.—Neither resistance nor susceptibility to diseases or pests has been observed in this variety.

Root system: Fine, fleshy roots; freely branched and moderately dense.

Stem:

*Branching habit*.—One primary flowering stem with numerous lateral branches which exhibit diminished inflorescences, potentially arising at any node along vegetative portion of the main stem.

*Main stem*.—Quantity Main Stems — One. Stem Length — Approximately 55 cm, excluding the inflorescence. Stem Width — Approximately 1.7 cm. Branch Aspect — Vertical. Stem Color — Near RHS 144A, and heavily tinged near RHS N186C. Stem Texture — Glabrous; smooth; glaucous. Internode Length — Observed length is 0.9 cm, but may vary depending on light levels.

*Lateral branches*.—Quantity of Lateral Branches — Approximately 8 lateral branches, as observed. Branch Length — Longest observed lateral branch measuring approximately 28 cm, excluding the inflorescence. Branch Width — Approximately 0.4 cm at the widest point of the longest observed lateral branch. Branch Aspect — Approximately 15 to 25 degrees from vertical. Branch Color — Near RHS 144A, and tinged near RHS N186C. Branch Texture — Glabrous; smooth; glaucous. Internode Length — Highly variable; longest internode length measuring approximately 12 cm.

Foliage:

*Leaf arrangement*.—Rosette at plant base and alternate along flowering stems.

*Leaf attachment*.—Petiolate.

*Quantity of leaves on the main stem*.—Approximately 35.

*Leaf length*.—Approximately 15 cm.

*Leaf width*.—Approximately 16 cm.

*Leaf shape*.—Palmately lobed; symmetrical.

*Leaf apex*.—Acute to acuminate.

*Leaf base*.—Reniform to hastate.

*Leaf margin*.—Incised.

*Texture* (*adaxial* & *abaxial surfaces*).—Smooth.

*Pubescence* (*adaxial surface*).—Glabrous.

*Leaf color* (*adaxial surface*).—Near RHS 137A.

*Leaf color* (*abaxial surface*).—Near RHS 138B.

*Venation*.—Pinnate.

*Vein color* (*adaxial surface*).—Near RHS 137B.

*Vein color* (*abaxial surface*).—Near RHS 138C.

*Petiole*.—Approximately 13.4 cm long and 0.4 cm wide; color is near 144A; texture is smooth; glabrous.

Inflorescence:

*Inflorescence type*.—Terminal raceme.

*Inflorescence dimensions*.—Approximately 40 cm long, as measured from the lowest flower to the apex of the inflorescence, and 10 cm wide.

*Peduncle*.—Length — Approximately 59.0 cm. Diameter — Approximately 0.7 cm. Color — Yellow-green, near RHS 148A, but slightly darker. Attitude — Erect, in an average angle of 0 degrees to the main stem. Strength — Very Strong.

*Bract*.—Quantity — Two bracts are present at the base of each pedicel. Shape — Linear. Length — 2.1 cm, on average. Width — 0.1 cm, on average. Apex — Narrowly acute. Margin — Entire. Color (adaxial and abaxial surfaces) — Near RHS 143A.

Bud:

*Flower bud shape*.—Orbicular to obovate.

*Flower bud length*.—2.5 cm, excluding the spur.

*Flower bud diameter*.—Averaging 2.0 cm.

*Bud color*.—Near RHS Purple 77A.

Flower:

*Flowering quantity*.—Approximately 30 florets per raceme.

*Natural glowering season*.—Naturally blooming continuously from early through late summer.

*Longevity on the plant*.13 Approximately 7 days.

*Longevity as a cut flower*.—Approximately 7 days under high temperatures; approximately 14 days under cool temperature.

*Pedicel*.—Length — Approximately 5.2 cm. Diameter — Approximately 0.15 cm. Texture — Smooth; glabrous. Color — Near RHS 143A and 147B, tinged N186C.

*Perianth*.—Consisting of a spur, a single whorl of tepals, and multiple whorls petaloids; the approximate diameter is 6.0 cm and the approximate depth is 2.1 cm, excluding the spur. Aspect of corolla is upward to slightly pendulous. Flowers are persistent.

*Tepal description*.—Arrangement — Rotate. Quantity — Five. Length — Approximately 3.1 cm. Width — Two lower tepals average 1.6 cm and three upper tepals average 2.0 cm. Shape — Obovate. Margin — Entire, undulate; sparsely covered with very thin short hairs with an average length of 0.1 cm; color of said hairs is near RHS N155D. Apex — Broad acute. Texture (adaxial and abaxial surfaces) — Glabrous, slightly glossy and slightly velvety. Aspect — Slightly curved backwards. Color, When Opening (adaxial surface) — Near RHS 84D; base and central stripe near RHS 146C. Color, When Opening (abaxial surface) — Near RHS 84C and 84D; base and central stripe near RHS 146C and a darker localized area or "dot" at the apex with color near RHS 146A. Color, Fully Opened (adaxial surface) — Near RHS 84D; base and central stripe near RHS 146C. Color, Fully Opened (abaxial surface) — Near RHS 84C and 84D; base and central stripe near RHS 146C and a darker localized area or "dot" at the apex with color near RHS 146A.

*Petaloid description*.—Quantity — Approximately 50. Arrangement — Whorled. Length — Approximately 2.5 cm. Width — Approximately 1.5 cm. Shape — Oblong. Margin — Entire to serrulate. Apex — Rounded. Base — Roughly obtuse. Texture (adaxial and abaxial surfaces) — Slightly velvety, slightly glossy, and glabrous. Color, When Opening (adaxial surface) — Near RHS Blue 100A. Color, When Opening (abaxial surface) — Near RHS Purple 77A. Color, Fully Opened (adaxial surface) — Near RHS Purple 77B, 78D and Blue 100A mixed with Yellow-Green 144A and 145A. Color does not fade. Color, Fully Opened (abaxial surface) — Near RHS Purple 77B, 78D and Blue 100A mixed with Yellow-Green 144A and 145A. Color does not fade.

*Spur*.—Shape — Oblong; narrow. Quantity per flower — 1. Length — Approximately 1.5 cm. Width — Approximately 0.3 cm. Texture — Smooth; glabrous. Color — Near RHS 84A.

Reproductive organs: All organs are fragmented due to the amount of tepals and petaloids, making the cultivar sterile.

Seed and fruit: Cultivar is sterile, no fruit or seed are produced.

COMPARISONS WITH THE PARENTS

Plants of the new cultivar 'Coadelcha' are similar to plants of the seed parent variety, an unnamed *Delphinium* hybrid, in most horticultural characteristics. However, flowers of the new variety have more petals, and a stronger, more consistent color.

Plants of the new cultivar 'Coadelcha' are similar to plants of the pollen parent variety, an unnamed *Delphinium* hybrid, in most horticultural characteristics. However, flowers of the new variety have more petals, and a stronger, more consistent color.

COMPARISONS WITH SIMILAR *DELPHINIUM* VARIETIES

Plants of the new cultivar 'Coadelcha' are similar to the cultivar, *Delphinium* 'Coadelbol' (co-pending U.S. Plant patent application Ser. No. 14/545,379). However, the claimed plant can be distinguished from 'Coadelbol' by several characteristics. A comparison of 'Coadelcha' with 'Coadelbol' is described in Chart 1.

CHART 1

| Characteristic | 'Coadelcha' | 'Coadelbol' |
|---|---|---|
| Color of main stem. | Near RHS 144A; heavily tinged near RHS N186C and covered by a thin, waxy layer colored greyed-green, near RHS 198A to 198C. | Green, near RHS 143A and 147B; covered with a thin, waxy layer colored greyed-green, near RHS 191D. |
| Color of peduncle. | Yellow-green, near RHS 148A, but slightly darker. | Green, near RHS 143A to 143B, but slightly darker. |
| Leaf length. | Shorter than those of 'Coadelbol'. | Longer than those of 'Coadelcha'. |
| Leaf width. | More narrow than those of 'Coadelbol'. | Wider than those of 'Coadelcha'. |
| Perianth diameter. | Larger in diameter. | Smaller in diameter. |
| Depth of perianth. | Deeper than the perianth of 'Coadelbol'. | More shallow than the perianth of 'Coadelcha'. |
| Tepal color when opening, adaxial surface. | Near RHS 84D; base and central stripe near RHS 146C. | Near RHS 98A and 99D; base and central stripe tinged near RHS 146B and 146C. |
| Tepal color when opening, abaxial surface. | Near RHS 84C and 84D; base and central stripe near RHS 146C and a darker localized area or "dot" at the apex with color near RHS 146A. | Near RHS 98A and 99D; base and central stripe tinged near RHS 146B and 146C. |
| Tepal color when fully open, adaxial surface. | Near RHS 84D; base and central stripe near RHS 146C. | Near RHS 99B; base and central stripe tinged near RHS 146C. |
| Tepal color when fully open, abaxial surface. | Near RHS 84C and 84D; base and central stripe near RHS 146C and a darker localized area or "dot" at the apex with color near RHS 146A. | Near RHS 98A and 99D; base and central stripe tinged near RHS 146B and 146C. |
| Petaloid color when fully open, adaxial surface. | Near RHS Purple 77B, 78D and Blue 100A mixed with Yellow-Green 144A and 145A. | Near RHS 95C and 85A, base and central stripe near RHS 145B to 145D. Those petaloids near the center of the perianth are colored near RHS 157D, base, central stripe and tip near 145B to 145D. |
| Petaloid color when fully open, abaxial surface. | Near RHS 77B, 78D and Blue 100A, mixed with Yellow-Green 144A and 145A. | Near RHS 95C and 85A, base and central stripe near RHS 145B to 145D. Those petaloids near the center of the perianth are colored near RHS 157D, base, central stripe and tip near 145B to 145D. |

Plants of the new cultivar 'Coadelcha' are also similar to the cultivar, *Delphinium* 'Coadelfla' (co-pending U.S. Plant patent application Ser. No. 14/545,380). However, the claimed plant can be distinguished from 'Coadelbol' by several characteristics. A comparison of 'Coadelfla' with 'Coadelbol' is described in Chart 2.

CHART 2

| Characteristic | 'Coadelcha' | 'Coadelfla' |
|---|---|---|
| Color of main stem. | Near RHS 144A; heavily tinged near RHS N186C and covered by a thin, | Near RHS 146A to 146B and covered with a thin, waxy layer colored yellow- |

CHART 2-continued

| Characteristic | 'Coadelcha' | 'Coadelfla' |
|---|---|---|
| | waxy layer colored greyed-green, near RHS 198A to 198C. | green, near RHS 147C to 147D. |
| Color of peduncle. | Yellow-green, near RHS 148A, but slightly darker. | Yellow-green, near RHS 148A. |
| Leaf length. | Longer than those of 'Coadelbol'. | Shorter than those of 'Coadelcha'. |
| Leaf width. | Wider than those of 'Coadelbol'. | More narrow than those of 'Coadelcha'. |
| Perianth diameter. | Larger in diameter. | Smaller in diameter. |
| Depth of perianth. | Deeper than the perianth of 'Coadelbol'. | More shallow than the perianth of 'Coadelcha'. |
| Tepal color when opening, adaxial surface. | Near RHS 84D; base and central stripe near RHS 146C. | Near RHS 76A; the base and also a darker localized area or "dot" at the apex with color near RHS 146A to 146B. |
| Tepal color when opening, abaxial surface. | Near RHS 84C and 84D; base and central stripe near RHS 146C and a darker localized area or "dot" at the apex with color near RHS 146A. | Slightly lighter than RHS N77D; the base and also a darker localized area or "dot" at the apex with color near RHS 146A. |

CHART 2-continued

| Characteristic | 'Coadelcha' | 'Coadelfla' |
|---|---|---|
| Tepal color when fully open, adaxial surface. | Near RHS 84D; base and central stripe near RHS 146C. | Near RHS 99B; base and central stripe tinged near RHS 146C. |
| Tepal color when fully open, abaxial surface. | Near RHS 84C and 84D; base and central stripe near RHS 146C and a darker localized area or "dot" at the apex with color near RHS 146A. | Near RHS 98A and 99D; base and central stripe tinged near RHS 146B and 146C. |
| Petaloid color when fully open, adaxial surface. | Near RHS Purple 77B, 78D and Blue 100A mixed with Yellow-Green 144A and 145A. | Near RHS 76A; the base and also a darker localized area or "dot" at the apex with color near RHS 146A to 146B. |
| Petaloid color when fully open, abaxial surface. | Near RHS 77B, 78D and Blue 100A, mixed with Yellow-Green 144A and 145A. | Slightly lighter than RHS N77D; the base and also a darker localized area or "dot" at the apex with color near RHS 146A. |

That which is claimed is:

1. A new and distinct variety of *Delphinium* plant named 'Coadelcha', substantially as described and illustrated herein.

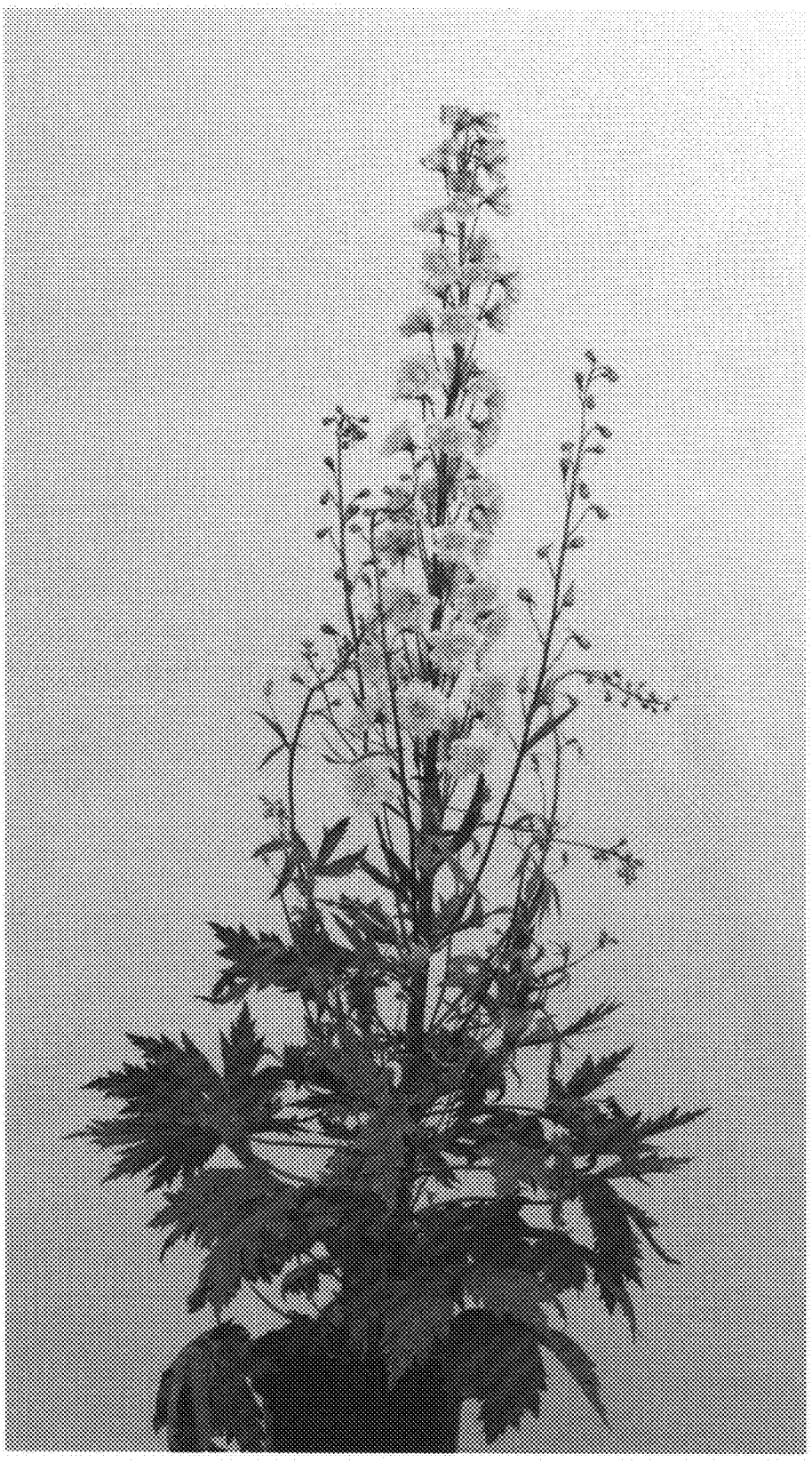

* * * * *